(12) United States Patent
Sipilä et al.

(10) Patent No.: US 9,916,972 B2
(45) Date of Patent: Mar. 13, 2018

(54) METHOD AND DEVICE FOR IONIZING PARTICLES OF A SAMPLE GAS FLOW

(71) Applicant: University of Helsinki, Helsinki (FI)

(72) Inventors: Mikko Sipilä, Helsinki (FI); Heikki Junninen, Helsinki (FI); Douglas Worsnop, Billerica, MA (US)

(73) Assignee: UNIVERSITY OF HELSINKI, Helsinki (FI)

( * ) Notice: Subject to any disclaimer, the term of this patent is extended or adjusted under 35 U.S.C. 154(b) by 130 days.

(21) Appl. No.: 14/897,690

(22) PCT Filed: Jun. 11, 2014

(86) PCT No.: PCT/FI2014/050470
§ 371 (c)(1),
(2) Date: Dec. 11, 2015

(87) PCT Pub. No.: WO2014/202828
PCT Pub. Date: Dec. 24, 2014

(65) Prior Publication Data
US 2016/0126079 A1    May 5, 2016

Related U.S. Application Data

(60) Provisional application No. 61/837,341, filed on Jun. 20, 2013.

(30) Foreign Application Priority Data

Jun. 20, 2013 (FI) ...................................... 20135681

(51) Int. Cl.
*H01J 49/10*    (2006.01)
*H01J 49/14*    (2006.01)
(Continued)

(52) U.S. Cl.
CPC ............ *H01J 49/145* (2013.01); *H01J 49/12* (2013.01); *H01J 49/26* (2013.01); *G01N 27/622* (2013.01); *H01J 49/0077* (2013.01)

(58) Field of Classification Search
CPC .......... H01J 49/145; H01J 49/12; H01J 49/26; H01J 49/0422; H01J 49/0077; G01N 27/622
See application file for complete search history.

(56) References Cited

U.S. PATENT DOCUMENTS 4,005,291 A    1/1977  Arsenault
5,175,431 A  * 12/1992  Eisele .................... G01N 30/06
                                                           250/282

(Continued)

FOREIGN PATENT DOCUMENTS

CN    1214528 A    4/1999
CN    1585666 A    2/2005
(Continued)

OTHER PUBLICATIONS

Mauldin, R. L., D. J. Tanner, and F. L. Eisele. "A new chemical ionization mass spectrometer technique for the fast measurement of gas phase nitric acid in the atmosphere." Journal of Geophysical Research: Atmospheres 103.D3 (1998): 3361-3367.*

(Continued)

*Primary Examiner* — Wyatt Stoffa
(74) *Attorney, Agent, or Firm* — Berggren Inc.

(57) ABSTRACT

A device for ionizing sample particles of a sample gas flow comprises a first flow tube for providing the sample gas flow, and an introducing means for providing $H_2SO_4$ molecules to an interaction region. In addition the device comprises a generator for producing reagent primary ions from particles of candidate reagent gas flow essentially in a primary ion production region. The device is configured to introduce said reagent primary ions with $H_2SO_4$ molecules in said interac- (Continued)

tion region in order to arrange interaction between the reagent primary ions and the $H_2SO_4$ molecules, thereby producing $HSO_4^-$ ions and again to produce $HSO4^-$ ion clusters comprising $HSO_4^-$ ions and at least two $H_2SO_4$ molecules via interactions of $HSO_4^-$ with other $H_2SO_4$ molecules in said interaction region. Furthermore the device is configured to introduce said $HSO_4^-$ ion clusters with the sample particles of the sample gas flow in order to provide reactions between said $HSO_4^-$ ion clusters and the sample particles, and thereby provide a sample cluster comprising the $HSO_4^-$ ion clusters and said base sample to be determined.

20 Claims, 1 Drawing Sheet

(51) Int. Cl.
*H01J 49/12* (2006.01)
*H01J 49/26* (2006.01)
*H01J 49/00* (2006.01)
*G01N 27/62* (2006.01)

(56) References Cited

U.S. PATENT DOCUMENTS

| | | | |
|---|---|---|---|
| 6,037,587 A | 3/2000 | Dowell et al. | |
| 8,319,194 B2* | 11/2012 | Hashimoto | H01J 49/04 250/282 |
| 2009/0095902 A1* | 4/2009 | Robinson | H01J 49/145 250/287 |
| 2009/0256073 A1 | 10/2009 | Guo et al. | |
| 2012/0131989 A1* | 5/2012 | Vanhanen | G01N 15/06 73/28.01 |
| 2014/0284204 A1* | 9/2014 | Sipila | B01J 19/125 204/157.44 |

FOREIGN PATENT DOCUMENTS

| | | |
|---|---|---|
| EP | 2086000 A2 | 8/2009 |
| JP | H05174782 A | 7/1993 |
| WO | 9216961 A1 | 10/1992 |
| WO | 9966536 A2 | 12/1999 |
| WO | 2013072565 A1 | 5/2013 |

OTHER PUBLICATIONS

The Intellectual Property Office of P.R. China, First Notification of Office Action and Search Report dated Oct. 27, 2016 issued on application No. CN201480035121.8.
Junninen H et al. 'A high-resolution mass spectrometer to measure atmospheric ion composition' In Atmos. Meas. Tech., Feb. 12, 2010.
Jokinen T et al. 'Atmospheric sulphuric acid and neutral cluster measurements using CI-APi-TOF' in Atmos. Chem. Phys., Dec. 6, 2011.
Bzdek BR et al. 'Amine reactivity with charged sulfuric acid clusters' in Atmos. Chem. Phys., May 12, 2011.
Kirkby J et al. 'Role of sulphuric acid, ammonia and galactic cosmic rays in atmospheric aerosol nucleation' in Nature, Aug. 25, 2011.
Weak base, Wikipedia article online May 8, 2012, retrieved on Apr. 4, 2014 from Internet.
FI20135681 Search report, Patentti-ja rekisterihallitus, Apr. 8, 2014.
Kurten T et al. 'The effect of H2SO4—amine clustering on chemical ionization mass spectrometry (CIMS) measurements of gas-phase sulfuric acid', Atmos. Chem. Phys., Dec. 15, 2010.

* cited by examiner

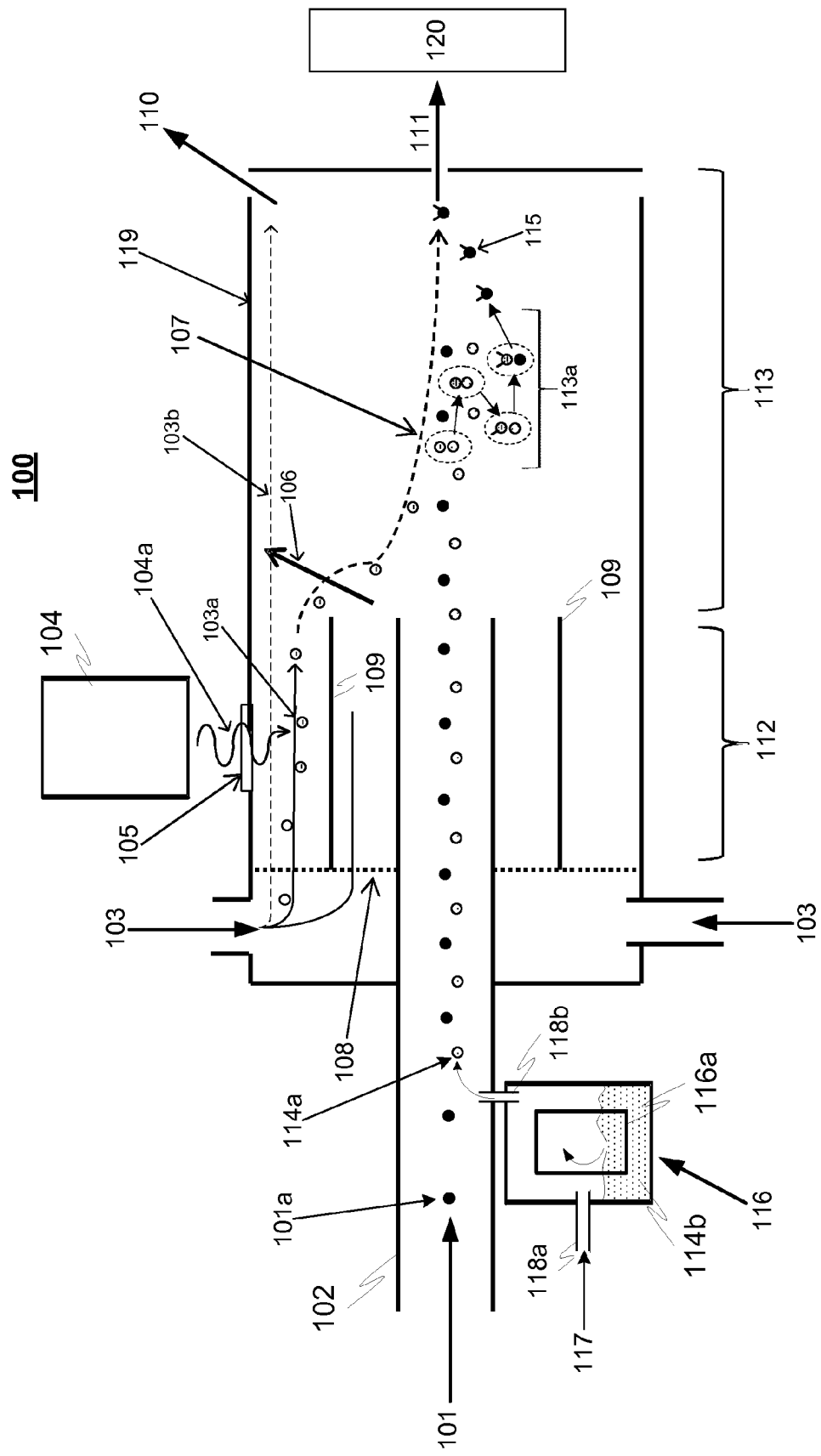

METHOD AND DEVICE FOR IONIZING PARTICLES OF A SAMPLE GAS FLOW

PRIORITY

This application is a national application of PCT-application PCT/FI2014/050470, filed on Jun. 11, 2014 and claiming priority of the US provisional application number U.S. 61/837,341 filed on Jun. 20, 2013 and of Finnish national application filed on Jun. 20, 2013, the contents of all of which are incorporated herein by reference.

TECHNICAL FIELD OF THE INVENTION

The invention relates to a method and device for ionizing particles of a sample gas flow before a detector, such as a mass spectrometer, in order to determine properties, such as masses or concentrations, of gas phase samples or especially molecules or clusters, for example gas phase bases, such as ammonia and especially amines.

BACKGROUND OF THE INVENTION

An accurate mass spectrometry methods for determining of properties of gas phase samples are in very important role e.g. in atmospheric studies, such as studying e.g. roles of different chemical substances, such as ammonia, amines, in atmospheric nanoparticle formation. Especially there is a need for better knowing or determination of low concentrations and variability of atmospheric ammonia and amines and highly oxidized organics, as an example. In addition very accurate methods for determining of properties of gas phase samples, such as amines, are needed also in other fields, such as in a medical industry and diagnostics, security and food processing industry.

However, measurement of trace amounts of gaseous compounds for example from air is extremely difficult, as their concentration is minimal compared to the total air molecule concentration, and due to the large variety of the different gases compounds and their isotopes. However, some of these molecules have a significant effect on the air chemistry and aerosol formation, even in small amounts. Therefore exact measurements are needed for instance in atmospheric aerosol research.

Very often gas phase samples are analysed by a mass spectrometer, but also other detecting devices can be used, such as IMS-device (Ion Mobility Spectrometry) or DMA-device (Differential Mobility Analyzers). The mass spectrometer is detecting the mass to charge ratio of an ion or ion cluster, whereas IMS and DMA devices are based on the electrical mobility of the sample particles. As majority of sample particles, such as airborne molecules and clusters are initially neutral, they need to be charged before a measurement.

One exemplary method to charge the sample particles, such as ammonia or amine molecules and clusters, before the measurement and thereby provide an ion flow of sample constituents is chemical ionizing (CI) of the sample constituents using an ionizer.

There are, however, some drawback related to known solutions namely particles to be determined may stick to inner wall structures of the ionizer and afterwards be released back to the sample gas flow and induce signal in a detector. Thus it is said that the wall structures of the ionizer has a memory effect (or wall effect). Anyway this is a very undesired feature because the particles are released very randomly and thus they will disturb the measurement at first by sticking into the structure and thereby reducing a signal to be measured, and secondly by releasing to the later sample flow and increasing the signal of the later sample flow to be detected.

SUMMARY OF THE INVENTION

An object of the invention is to alleviate and eliminate the problems relating to the known prior art. Especially the object of the invention is to provide a method and device for ionizing particles of a sample gas flow for detection of extremely low concentrations of gas phase constituents, comprising especially ammonia and amines. In particularly the object is to eliminate the wall effects so that the sample particles are not inducing undesired signals and interfering measurements.

The object of the invention can be achieved by the features of independent claims. The invention relates to a method according to claim 1. In addition the invention relates to a device according to claim 11, and to an arrangement according to claim 19.

According to an embodiment of the invention particles, such as molecules or clusters, of a sample gas flow is ionized by an ionizer so that properties of the sample gas flow particles can be determined. The particles comprise advantageously base molecules or clusters, such as ammonia or amines. According to the embodiment $H_2SO_4$ molecules are provided to an interaction region. The $H_2SO_4$ molecules may be exist e.g. in the form of vapour. In addition reagent primary ions are generated from particles of candidate reagent gas flow in a primary ion production region. Said candidate reagent gas flow may comprise $HNO_3$ (nitric acid), $CH_3COOH$ (acetic acid), $CH_3I$ (methyliodide), $H_2SO_4$, $O_2$, as an example whereupon said reagent primary ions may comprise e.g. $NO_3-$, $I-$ (iodide), $CH_3COO-$ (acetate ion), $O_2-$, or even $HSO_4^-$ as an example. The reagent primary ions can be produced e.g. by ionising said particles of the candidate reagent gas flow using soft X-ray radiation or ionising radiation by an $\alpha$ source for example or a corona discharge source. The sample particles are typically bases or strong bases, like ammonia and amines, stuff like pyridine, quinoline, aniline, or highly oxidized organic molecules. It is to be understood that these are only examples and also other candidate reagent gas flow can be used for generation of also other reagent primary ions.

Said reagent primary ions are advantageously introduced with said $H_2SO_4$ molecules in said interaction region in order to arrange interaction between the reagent primary ions and the $H_2SO_4$ molecules. When said reagent primary ions and the $H_2SO_4$ molecules interacts $HSO_4-$ ions are produced. Again when said $HSO_4-$ ions are interacted with other $H_2SO_4$ molecules e.g. in said interaction region, $HSO_4-$ ion clusters comprising $HSO_4-$ ions and least two $H_2SO_4$ molecules are generated (=$H_2SO_4.H_2SO_4.HSO_4-$ or $H_2SO_4.H_2SO_4.H_2SO_4.HSO_4-$ etc. . . . ) via interactions of $HSO_4-$ with other $H_2SO_4$ molecules Again said $HSO_4-$ ion clusters are introduced with the sample particles, like amines, of the sample gas flow in order to provide reactions between said $HSO_4-$ ion clusters and the sample particles, and thereby provide a sample cluster comprising the $HSO_4-$ ion clusters and said base sample, which can be determined by a suitable detector, such as an APi-TOF mass spectrometer quadrupole MS, ion trap MS, or ion mobility analyser.

According to an example said $H_2SO_4$ molecules can be introduced to the sample gas flow before introduction to the interaction region in order to provide a mixed sample gas flow (having both H2SO4 and the sample particles, such as amines). Said H2SO4 molecules are introduced from a H2SO4 providing means, such as a saturator comprising H2SO4 vapour.

In addition a sheath flow may be arranged to flow at least through a primary ion production region and/or said interaction region between the sample gas flow and structure of said ionizer. The sheath flow is e.g. clean air or nitrogen, possibly with small amounts of reagent gas molecules, e.g. nitric acid, sulphuric acid, acetic acid, methyl iodide, oxygen, ammonia, amines, alcohols, or acetone.

According to an embodiment the sample gas flow and candidate reagent gas flow may be configured to flow essentially concentrically at the primary ion production regions. In addition the trajectory of the produced reagent primary ions is advantageously configured to bend inward and towards the sample gas flow and said H2SO4 molecules in order to provide effective interactions especially between said H2SO4 molecules and said reagent primary ions. The trajectory of the produced reagent ions can be achieved for example by using an electric field for attracting or repulsing said ions, and/or by using flow current guiding means, such as a deflector, wing or throttle, like a venturi tube, for example.

The ionizing process of the embodiments of the invention is advantageously implemented essentially at atmospheric pressure.

The invention offers remarkable advantages over the known prior art solutions, namely because the inner walls and structures of the ionizer are heavily saturated by H2SO4 and/or other acids (e.g. HNO3), the possible "wall effects" can be controlled. Any possible base particles interacted with the saturated inner walls and structures are not able to drift back to the sample flow because bases when interacting with the acids at the wall/structure form salts, which are non-vaporizable and thus not able to interfere the measurements afterwards.

The exemplary embodiments presented in this text are not to be interpreted to pose limitations to the applicability of the appended claims. The verb "to comprise" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which:

FIG. 1 illustrates a principle of an exemplary device for ionizing particles of a sample gas flow according to an advantageous embodiment of the invention.

DETAILED DESCRIPTION

FIG. 1 is a principle-level schematic illustration of both a method and a device 100 for ionizing particles of a sample gas flow according to an advantageous embodiment of the invention. The device 100 comprises an inlet, which can be in the form of a first flow tube 102 for providing the sample gas flow 101. In addition the device comprises a generator 104 for producing reagent primary ions 103a from particles of candidate reagent gas flow 103 essentially in a primary ion production region 112 (region where the ionizing radiation ionizes the candidate reagent gas flow 103). The generator 104 may be an X-ray radiation or α-radiation source or a corona discharge source, as an example. These are only examples and also other types of sources can be used, such as β-radiation source.

In addition the device comprises also providing means 116 for providing and introducing H2SO4 molecules, preferably vapour, 114a to an interaction region 113. The H2SO4 providing means is advantageously a saturator 116, but also other types of providing means can be applied, such as a device with a space for SO2+H2O solution with a radiation source, such as UV radiation source to produce H2SO4 vapour. A carrier medium 117, such as N2 flow, is advantageously used for carrying 118a, 118b said H2SO4 molecules to the interaction region 113.

According to an example the saturator 116 as the providing means comprises a rotating means 116a, which is immersed at least partially into H2SO4 medium 114b. The rotating means advantageously rotates and thereby introduce fresh H2SO4 medium for the carrier medium 117 and thereby saturates the carrier medium 117 with H2SO4 when said carrier medium is flown 118a, 118b through the saturator.

It is to be noted that said H2SO4 molecules 114a can be introduced by the providing means 116 to the sample gas flow 101 before the interaction region 113 in order to provide a mixed sample comprising said H2SO4 vapour and the particles, such as ammonia or amines, to be determined (as is described in FIG. 1), whereupon the gas flow with said H2SO4 vapour and the particles are introduced to the interaction region 113.

The device is configured to introduce said reagent primary ions with H2SO4 molecules 114a in said interaction region 113 in order to arrange interaction between the reagent primary ions 103a and the H2SO4 molecules 114a, thereby producing $HSO_4^-$ ions and again to produce $HSO_4^-$ ion clusters comprising $HSO_4^-$ ions and at least two H2SO4 molecules (i.e. H2SO4.H2SO4.HSO4– or H2SO4.H2SO4.H2SO4.H2SO4– etc. . . . ) via interactions of $HSO_4^-$ with other H2SO4 molecules in said interaction region 113.

In addition, the device may comprise also a laminarizer 108 for producing an essentially laminar sheath flow 103b between the reagent primary ions flow 107 and structure 119 of the device 100 and/or said second tube 109 in order to prevent or minimize the interaction between the structure of the device and the produced reagent primary ion flow.

It is to be noted, that according to an embodiment the device may additionally comprise a second flow tube 109 for producing a sheath flow 103b to flow at least through a primary ion production region 112 and/or said interaction region 113 between the sample gas flow 101 and inner wall structure 119 of the device, and thereby preventing or at least minimizing any interactions of the sample and/or reagent ions flow with the wall structure 119 of the ionizer 100. The first 102 and second 109 tubes may advantageously be arranged essentially concentrically in order to arrange said sample gas flow and candidate reagent gas flow to flow essentially concentrically at the primary ion production region. The sheath flow is advantageously essentially laminar flow, and it comprises e.g. clean air or nitrogen, with small amounts of reagent gas molecules, e.g. nitric acid, sulphuric acid, acetic acid methyl iodide or oxygen.

The device is advantageously also configured to bend the trajectory 107 of the produced reagent primary ions 103a inward and towards the mixed sample gas flow and/or H2SO4 molecules 114a by the means of electric field 106 produced by suitable electrodes and/or a flow current guiding means, such as a deflector, wing or throttle, like a venturi tube (not shown). According to an embodiment the electrode may be a separate electrode or it may be implemented via the second flow tube 109, which may comprise at least portion of it to function as an electrode and generating an electric field 106 and is thereby configured to bend the trajectory 107 of the produced reagent primary ions inward and towards the sample gas flow 101.

The device 100 as it simplest does not necessary comprise any detecting means 120. Anyhow, in order to also detect the samples ionized by the device 100, the device may be provided with a suitable detector, such as APi-TOF mass spectrometer quadrupole MS, ion trap MS, or ion mobility analyser, for example.

The device may also comprise a shielded area 105 between the X-ray or other radiation source 104 and the flowing media 103 (such as candidate reagent gas flow 103 and sheath flow 103a) for shielding the radiation source about any possible contamination of sample or other particles presented in the flow tubes. The shielded area 105 comprises advantageously beryllium, aluminum or glass, when the radiation source 104 is the X-ray source.

In addition the device may comprise also a laminarizer 108 for producing an essentially laminar sheath flow 103a between the reagent primary ions flow 107 and structure 115 of the device 100 and/or said second tube 109 in order to prevent or minimize the interaction between the structure of the device and the produced reagent primary ion flow.

Moreover, the device may comprise also an outlet channel 110 at the downstream portion of the device for removing the excess flow before the detector to be coupled with the device. The device may also comprise an adjusting means (not shown) for adjusting the flow rates of sample gas flow, candidate reagent gas flow and/or the sheath flow; as well as adjusting means for adjusting the current and/or voltage of the used X-ray source.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims.

The invention claimed is:

1. A method for ionizing sample particles of a sample gas flow by an ionizer, wherein the particles comprise base molecules or clusters, wherein the method comprises following steps:
    a) providing $H_2SO_4$ molecules to an interaction region,
    b) producing reagent primary ions from particles of candidate reagent gas flow in a primary ion production region,
    c) introducing said reagent primary ions with $H_2SO_4$ molecules in said interaction region in order to arrange interaction between the reagent primary ions and the $H_2SO_4$ molecules, thereby producing $HSO_4^-$ ions and again to produce $HSO4^-$ ion clusters comprising $HSO_4^-$ ions and least two $H_2SO_4$ molecules via interactions of $HSO_4^-$ with other $H_2SO_4$ molecules in said interaction region, and
    d) introducing said $HSO_4^-$ ion clusters with the sample particles of the sample gas flow in order to provide reactions between said $HSO_4^-$ ion clusters and the sample particles, and thereby provide a sample cluster comprising the $HSO_4^-$ ion clusters and said base sample to be determined.

2. The method according to claim 1, wherein said $H_2SO_4$ molecules are introduced to the sample gas flow before introduction to the interaction region in order to provide a mixed sample gas flow to be introduced to said interaction region.

3. The method according to claim 2, wherein said $H_2SO_4$ molecules are introduced from a saturator comprising $H_2SO_4$ vapour by using carrier medium, said carrier medium comprising $N_2$ flow carrying said $H_2SO_4$ molecules to said interaction region.

4. The method according to claim 1, wherein said reagent primary ions are produced by ionising said particles of the candidate reagent gas flow using soft X-ray radiation or ionising radiation by an α-source or a corona discharge source.

5. The method according to claim 1, wherein said candidate reagent gas flow comprises $HNO_3$, $CH_3COOH$ (acetic acid), $CH_3I$ (methyliodide), $H_2SO_4$, or $O_2$, and said reagent primary ions are $NO_3^-$ ions, $I^-$ (iodide), $CH_3COOH^-$ (acetate), $O_2^-$, or $HSO_4^-$, and wherein said sample bases are bases selected from the group consisting of ammonia, amines, pyridine, quinoline, aniline, and highly oxidized organic molecules.

6. The method according to claim 4, wherein the energy of the used soft X-ray photons is in a range of 1-10 keV.

7. The method according to claim 1, wherein a sheath flow is arranged to flow at least through a primary ion production region or said interaction region between the sample gas flow and structure of said ionizer, and wherein said sheath flow comprises clean air or nitrogen, with small amounts of reagent gas molecules selected from the group consisting of nitric acid, sulphuric acid, acetic acid, methyl iodide, oxygen, ammonia, amines, alcohols, and acetone.

8. The method according to claim 1, wherein the sample gas flow and candidate reagent gas flow is configured to flow essentially concentrically at the primary ion production regions, or wherein the trajectory of the produced reagent primary ions is configured to bend inward and towards the sample gas flow at the interaction region.

9. The method of claim 8, wherein the trajectory of the produced reagent ions are achieved by using an electric field or by using flow current guiding means, said flow current guiding means comprising a deflector, wing or throttle.

10. The method according to claim 1, wherein the ionizing process is implemented essentially at atmospheric pressure.

11. A device for ionizing sample particles of a sample gas flow, wherein the particles comprise base molecules or clusters, and wherein the device comprises:
    a first flow tube for providing the sample gas flow;
    an introducing member for providing $H_2SO_4$ molecules to an interaction region, said introducing member being a saturator or a device with a space for $SO_2+H_2O$ solution with a radiation source to produce H2SO$_4$ vapour;
    a generator for producing reagent primary ions from particles of candidate reagent gas flow essentially in a primary ion production region;
    wherein said device for ionizing sample particle of a sample gas flow is configured to:
        introduce said reagent primary ions with $H_2SO_4$ molecules in said interaction region in order to arrange interaction between the reagent primary ions and the $H_2SO_4$ molecules, thereby producing $HSO_4^-$ ions and again to produce $HSO4^-$ ion clusters comprising $HSO_4^-$ ions and at least two $H_2SO_4$ molecules via interactions of $HSO_4^-$ with other $H_2SO_4$ molecules in said interaction region, and introduce said $HSO_4^-$ ion clusters with the sample particles of the sample gas flow in order to provide reactions between said $HSO_4^-$ ion clusters and the sample particles, and thereby provide a sample cluster comprising the $HSO_4^-$ ion clusters and said base sample to be determined.

12. The device of claim 11, wherein the device is configured to introduce said $H_2SO_4$ molecules to the sample gas flow before the interaction region in order to provide a mixed sample gas flow to be introduced to said interaction region.

13. The device of claim 12, wherein the introducing member is a saturator, and wherein the device is configured to use carrier medium for carrying said $H_2SO_4$ molecules to said interaction region.

14. The device of claim 13, wherein the saturator is configured for producing $H_2SO_4$ molecules by manipulating $SO_2+H_2O$ solution with a radiation source.

15. The device of claim 13, wherein the saturator comprises a rotating means immersed at least partially into $H_2SO_4$ fluid and configured to transfer $H_2SO_4$ from the saturator and thereby to saturate the carrier medium with $H_2SO_4$ when said carrier medium is flown through the saturator.

16. The device of claim 11, wherein the device comprises an X-ray radiation or α-radiation source or a corona discharge source as a generator for producing said reagent primary ions.

17. The device of claim 11, wherein the device comprises a second flow tube for producing a sheath flow to flow at least through a primary ion production region or said interaction region between the sample gas flow and inner wall structure of the device.

18. The device of claim 11, wherein the device is configured to bend the trajectory of the produced reagent primary ions inward and towards the mixed sample gas flow or $H_2SO_4$ molecules by an electrode or a flow current guiding member comprising a deflector, wing or throttle.

19. An arrangement comprising a detector and a device for ionizing sample particles of a sample gas flow, wherein the particles comprise base molecules or clusters, and wherein the device comprises:

a first flow tube for providing the sample gas flow, introducing member for providing $H_2SO_4$ molecules to an interaction region, a generator selected from the group consisting of X-ray radiation source, α-radiation source, β-radiation source, and a corona discharge source for producing reagent primary ions from particles of candidate reagent gas flow essentially in a primary ion production region, wherein said device is configured to:

introduce said reagent primary ions with $H_2SO_4$ molecules in said interaction region in order to arrange interaction between the reagent primary ions and the $H_2SO_4$ molecules, thereby producing $HSO_4^-$ ions and again to produce $HSO4^-$ ion clusters comprising $HSO_4^-$ ions and at least two H2SO4 molecules via interactions of $HSO_4^-$ with other $H_2SO_4$ molecules in said interaction region, and introduce said $HSO_4^-$ ion clusters with the sample particles of the sample gas flow in order to provide reactions between said $HSO_4^-$ ion clusters and the sample particles, and thereby provide a sample cluster comprising the $HSO_4^-$ ion clusters and said base sample to be determined and wherein said sample cluster comprising the $HSO_4^-$ ion clusters and said base sample produced by said device is introduced to said detector for determination.

20. The arrangement of claim 19, wherein said detector is an APi-TOF mass spectrometer quadrupole MS, ion trap MS, or ion mobility analyser.

* * * * *